United States Patent
Kushibiki et al.

Patent Number: 5,688,961
Date of Patent: Nov. 18, 1997

[54] METHOD OF MANUFACTURING A SILICON-TYPE CHARGE TRANSPORTING MATERIAL

[75] Inventors: Nobuo Kushibiki; Kikuko Takeuchi, both of Kanagawa, Japan

[73] Assignee: Dow Corning Asia, Ltd., Tokyo, Japan

[21] Appl. No.: 740,738

[22] Filed: Nov. 4, 1996

[30] Foreign Application Priority Data

Nov. 6, 1995  [JP]  Japan ..................... 7-287644

[51] Int. Cl.$^6$ ..................... C07F 7/08; C07F 7/10; G03G 13/05
[52] U.S. Cl. ............ 548/955; 548/962; 556/407; 556/413; 556/424; 556/465; 430/59; 430/76; 430/78
[58] Field of Search ............ 430/58, 59, 76, 430/78, 127; 548/955, 962; 556/407, 413, 424, 465, 434

[56] References Cited

U.S. PATENT DOCUMENTS 4,752,549  6/1988  Otsuka et al. .
5,272,029  12/1993  Sakai et al. .

FOREIGN PATENT DOCUMENTS 4346356  2/1991  Japan .
61238062  3/1994  Japan .

*Primary Examiner*—Johann Richter
*Assistant Examiner*—Jane C. Oswecki
*Attorney, Agent, or Firm*—James L. Decesare

[57] ABSTRACT

A method of manufacturing charge transporting materials which impart a charge transporting property to a polysiloxane resin, and which is soluble in the resin. The charge transporting material is an aromatic substituted tertiary amine with a plurality of aromatic groups, and a silyl group introduced via a hydrocarbon group, into at least one of the aromatic groups. The method is characterized by using an unsaturated aliphatic group bonded to an aromatic group which makes up the silicon-type charge transporting compound, or using a newly bonded unsaturated aliphatic group which is bonded to a silane in which the substituent for silicon is hydrogen or a hydrolyzable group. This is conducted in the presence of a platinum compound as catalyst by means of hydrosilylation. The silicon-type charge transporting material is then brought into contact with an adsorbent for the platinum compound, causing the platinum compound to be adsorbed onto the adsorbent. The platinum compound is removed along with the adsorbent, so that the concentration of residual platinum compound is less than 10 ppm.

12 Claims, No Drawings

METHOD OF MANUFACTURING A SILICON-TYPE CHARGE TRANSPORTING MATERIAL

BACKGROUND OF THE INVENTION

This invention relates to new charge transporting substances used in electrophotographic organic photoconductor.

Electrophotographic organic photoconductor utilizing organic photoconductive materials have been attracting attention from the standpoint of productivity, facility of material design, and safety. They have undergone various improvements and are in use. In recent years, the configuration referred to as function-separation type, in which the layer which generates electric charge and the layer which transports charge are separated, has been proposed and put to use. An electrophotographic organic photoconductor with this configuration has two layers. One layer is composed of the electric charge generating material to an appropriate resin as binding agent. Another layer above this is the charge transporting material dispersed or dissolved in a binder resin. The layer containing the charge transporting material, and a binder which is a thermoplastic resin such as a polycarbonate resin, polyester resin, acrylic resin, and polystyrene resin; or a thermosetting resin such as a polyurethane resin or epoxy resin. In this case, it is necessary to apply a negative charge through a corona discharge device to the surface of the transporting layer. However, this process generates ozone which causes degradation of the resin, reduces sensitivity, and reduces electrostatic chargeability of the resin, which also leads to damage in the subsequent process of development, transfer of a latent image onto paper, and friction generated during cleaning The reduction in properties of the organic photoconductor caused by such factors has been a persistent problem.

Various studies have been conducted regarding these problems. For example, various attempts have been made to blend the polysiloxane resin with either a copolymer constituent or another resin, as seen in the use of a thermosetting polysiloxane resin as the charge transporting layer (i.e., Japanese Laid-Open Patent Application Kokai 61-238062); the use of a protective layer containing a polysiloxane resin (i.e., Japanese Laid-Open Patent Application Kokai 62-108260); the use of a protective layer of a thermosetting polysiloxane resin in which silica gel, urethane resin, and/or a polytetrafluoroethylene have been dispersed (i.e., Japanese Laid-Open Patent Application Kokai 4-346356); and the use of a thermoplastic resin in which a thermosetting polysiloxane resin has been dispersed as a protective layer or as a charge transporting material binder resin (i.e., Japanese Laid-Open Patent Application Kokai 4-273252). Studies have also been made to improve the performance, extend the life, and improve the cleaning property of photosensitive bodies by utilizing the properties of a polysiloxane.

Polysiloxane resins possess desirable characteristics such as transparency, ability to withstand dielectric breakdown, photostability, and low surface tension, which are characteristics not seen in other resins. But because they are compatible with organic compounds, they are not used alone as the resin constituting the charge transporting material. Rather, polysiloxane resins are used to improve the quality of the resin making up the charge transport material through copolymerization or blending. In order for polysiloxane resins to be used alone as the binder making up the charge transporting layer, it is necessary that a charge transporting substance be dissolved in the polysiloxane resin. Thus, the purpose of our invention is to provide a method of manufacturing such a charge transporting substance which can be dissolved in the polysiloxane resin, and impart the charge transporting property to the resin used in an electrophotographic organic photoconductor.

BRIEF SUMMARY OF THE INVENTION

Our invention relates to a method of manufacturing a silicon-type charge transporting material which is an aromatic substituted tertiary amine with a plurality of aromatic groups. The material has a silyl group introduced via a hydrocarbon group into at least one of the aromatic groups of the compound with charge transporting property and an ionization potential within the range of 4.5–6.3 eV. The method is characterized by using an unsaturated aliphatic group which is bonded to the aromatic group which makes up the silicon-type charge transporting compound, or using a newly bonded unsaturated aliphatic group which is then bonded to a silane in which the substituent for the silicon atom is hydrogen or a hydrolyzable group. This is carried out in the presence of a catalyst such as a platinum compound by means of a hydrosilylation reaction. The produced silicon-type charge transporting material is then brought into contact with an adsorbent for the platinum compound, causing the platinum compound to be adsorbed onto the adsorbent. The platinum compound is removed along with the adsorbent, so that the concentration of residual platinum compound is less than 10 ppm.

These and other features and objects of the invention will become apparent from a consideration of the detailed description.

DETAILED DESCRIPTION

The silicon-type charge transporting material of our invention is an aromatic substituted tertiary amine with a plurality of aromatic groups, and a silyl group is introduced via a hydrocarbon group into at least one of the aromatic groups of the compound. The compound with charge transporting properties has an ionization potential within the range of 4.5–6.2 eV and is a compound of the formula:

$$A-[R^1SiR^2{}_{3-n}Q_n]_p$$

where A is an aromatic substituted tertiary amine which has a plurality of aromatic groups, and represents an organic group derived from a compound having charge transporting properties with an ionization potential within the range of 4.5–6.2 eV; $R^1$ is an alkylene group of 1–18 carbon atoms; $R^2$ is a monovalent hydrocarbon group or a monovalent halogen-substituted hydrocarbon group of 1–15 carbon atoms; Q is a hydrolyzable group; n and p are each integers from 1–3. The silicon-type charge transporting material is characterized in that it represents an aromatic substituted tertiary amine which has a plurality of aromatic groups, a silyl group which is hydrolyzable, and the silyl group is introduced via a hydrocarbon group into an aromatic ring of at least one of the aromatic groups of the compound with the charge transporting properties with the ionization potential of 4.5–6.2 eV.

As used herein, the term "derived" refers to deriving by means of removal of a hydrogen atom or the substituent from the aromatic ring of the charge transporting compound.

Examples of hydrolyzable group Q include hydroxyl, methoxy, ethoxy, butoxy, methylethylketo oxime, diethylamino, acetoxy, propenoxy, propoxy, and Cl. Of these groups, hydroxyl and the alkoxy group, especially alkoxy groups with 1–6 carbon atoms, are preferable.

Silicon-type charge transporting compounds according to our invention have an ionization potential of 4.5–6.2 eV.

When the ionization potential is less than 4.5 eV, the silicon-type charge transporting material is easily oxidized and deteriorated making it undesirable. When the ionization potential exceeds 6.2 eV, injection of charge from the electric charge generating layer is inhibited, resulting in decreased sensitivity making it undesirable. The ionization potential in our invention was measured by open-air photoelectric spectrometry using surface analyzer AC-1 manufactured by Riken Keiki.

In the silicon-type charge transporting material provided by our invention, the organic silicon group is bonded to an electron-donor group via a hydrocarbon group. The reason is that if it is bonded directly, the π electron of the aromatic group in the charge transporting ring material is affected by the π-d interaction with the d electron of silicon; changing the ionization potential from that of the base material. Bonding via a hydrocarbon group prevents this phenomenon and facilitates designing of the organic photoconductor.

One method of including a hydrocarbon group between an aromatic ring and a silicon atom is to bond an unsaturated aliphatic group to at least one of multiple aromatic rings in the charge transporting compound, with an alkoxysilane whose essential substituent for the silicon atom is hydrogen and an alkoxy group, by means of a hydrosilylation reaction. For example, the silicon-type charge transporting material may be manufactured by means of a hydrosilylation reaction between a vinyl group substituted onto an aromatic ring bonded to nitrogen of an aromatic substituted tertiary amine whose ionization potential is 4.5–6.2 eV, and an organic silicon compound with a hydrogen bonded to silicon. One method of introducing the vinyl group to the aromatic group is to first formylate the hydrogen or the methyl group on the aromatic ring, then convert the resulted aldehyde group to the vinyl group by the Wittig reaction, thus introduction of the vinyl group. After this process, the hydrosilylation reaction can be employed. One of other method would be to bromomethylate a saturated hydrocarbon group such as methyl, which has been substituted onto the aromatic group, producing a lithocomplex, and then reacting this with a halogenated alkoxysilane.

The aromatic substituted tertiary amine A with an ionization potential of 4.5–6.2 eV used in the method of our invention may constitute any of the compounds shown below, where Me is methyl, Et is ethyl, Ph is phenyl, Bu is butyl, and Pr is propyl.

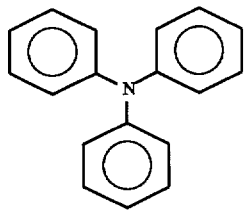

1A

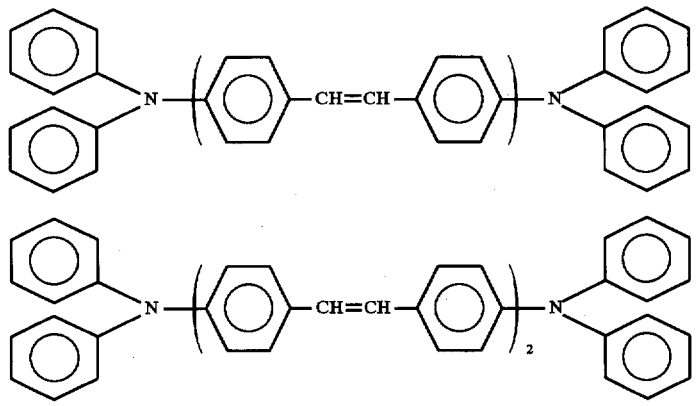

1B

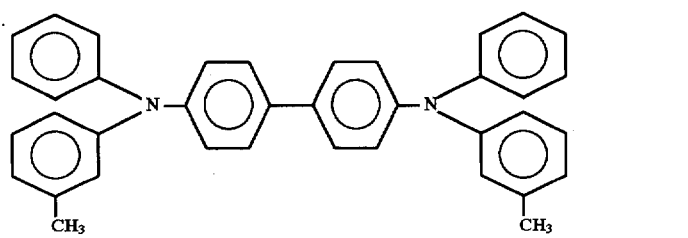

1C

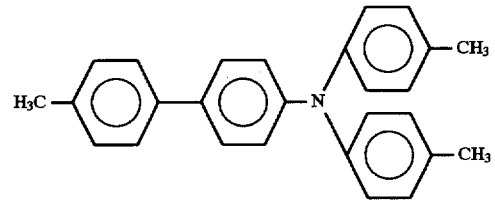

-continued
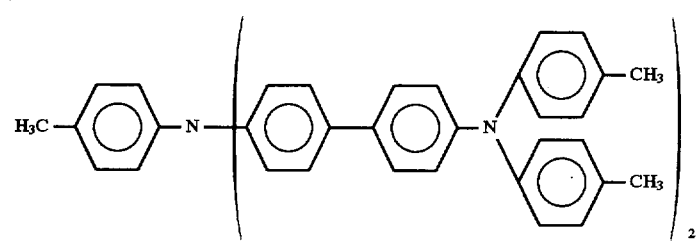
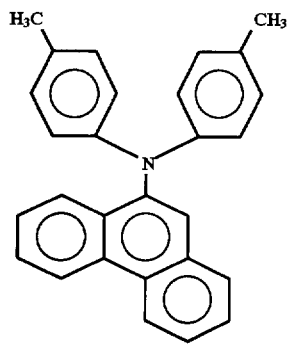
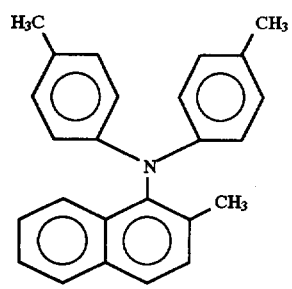
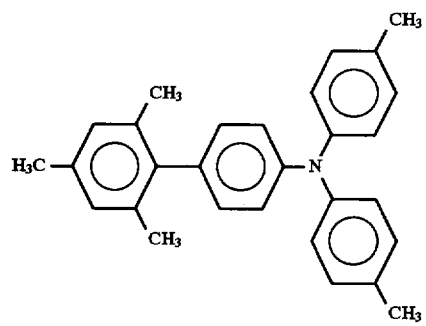
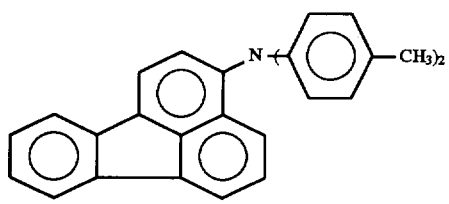
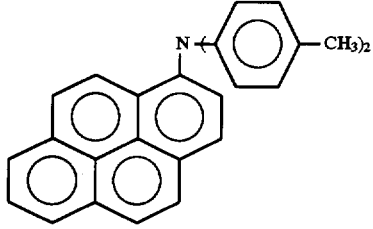

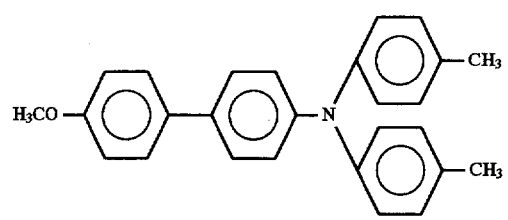
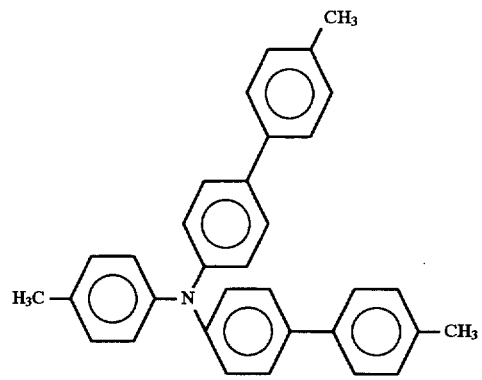
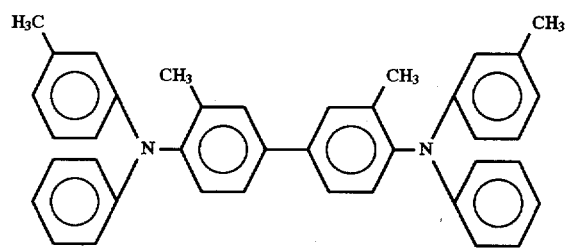
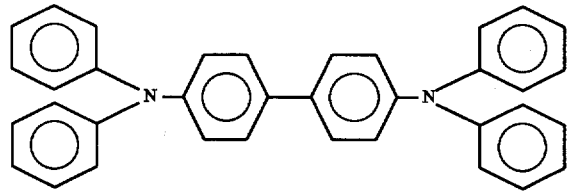
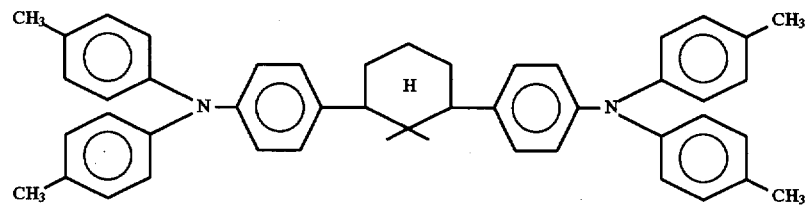
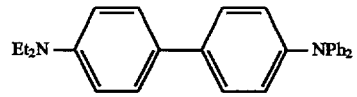
5A
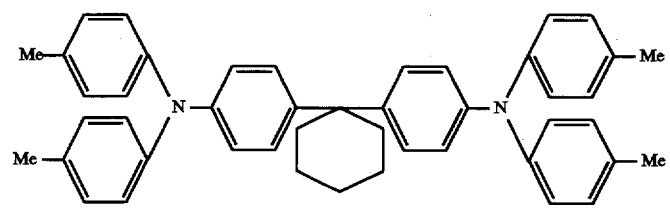
5B -continued
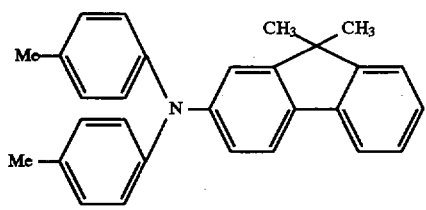
5C
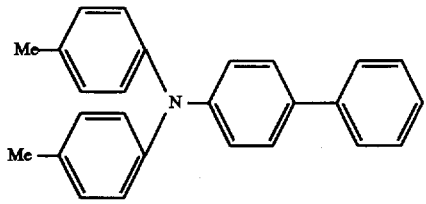
5D
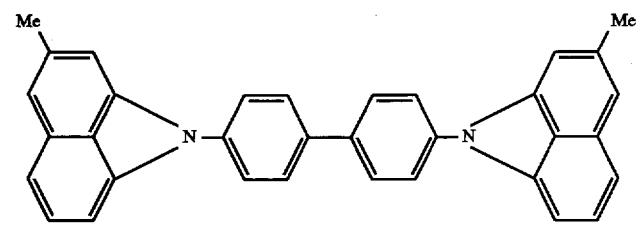
6A
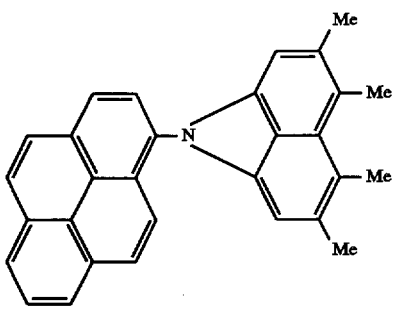
6B
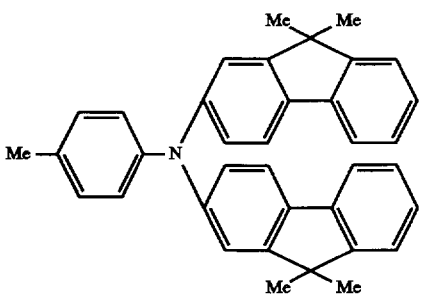
6C
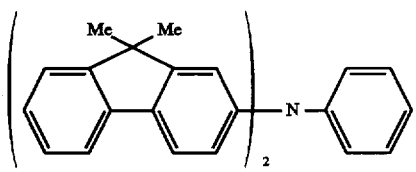
6D -continued
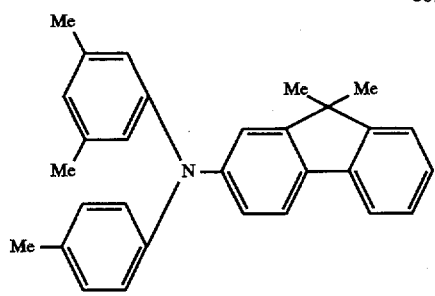
7A
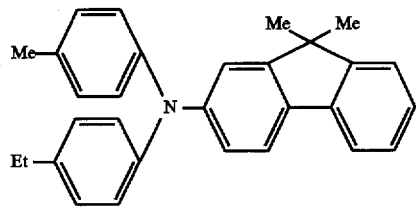
7B
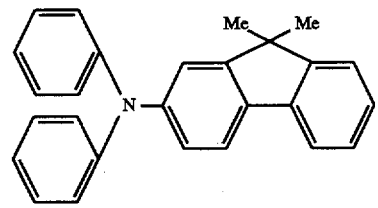
7C
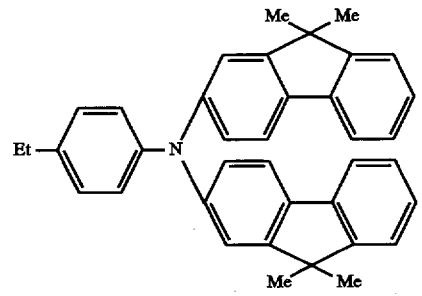
8A
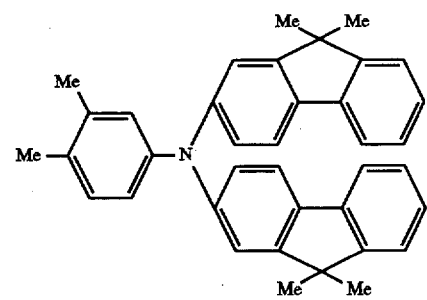
8B
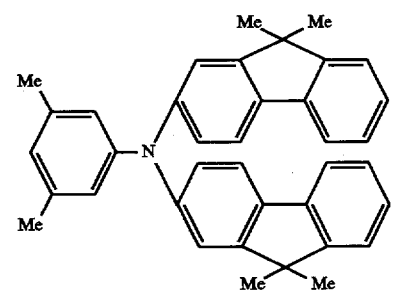
8C -continued
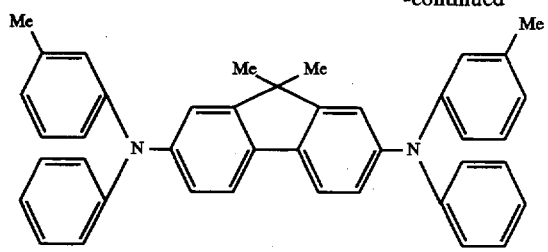
9A
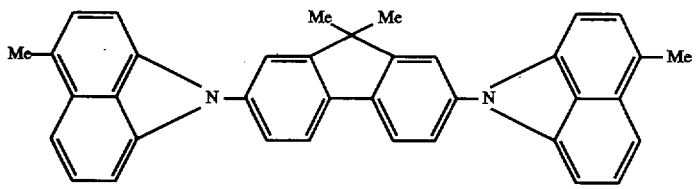
9B
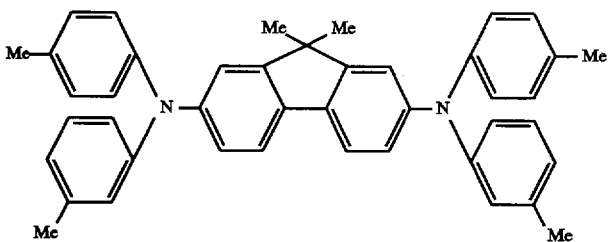
9C
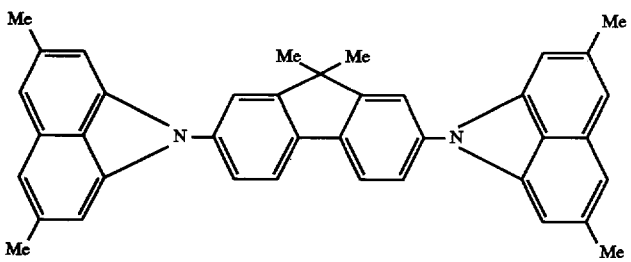
9D
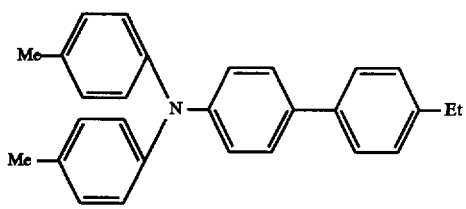
10A
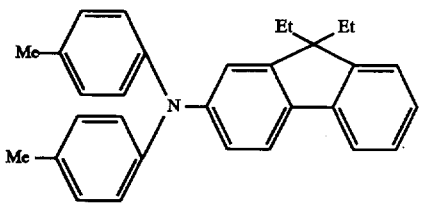
10B
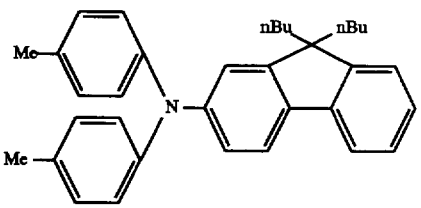
10C

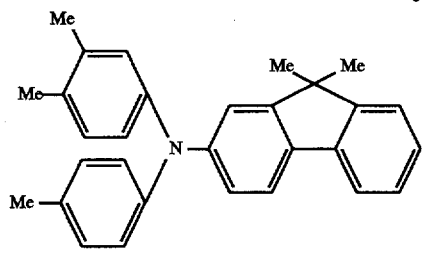
10D
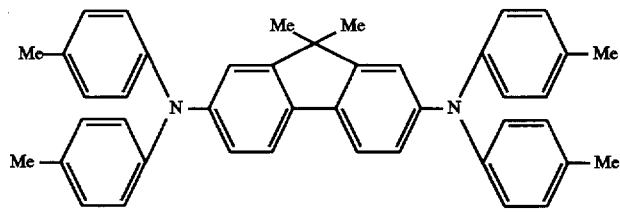
11A
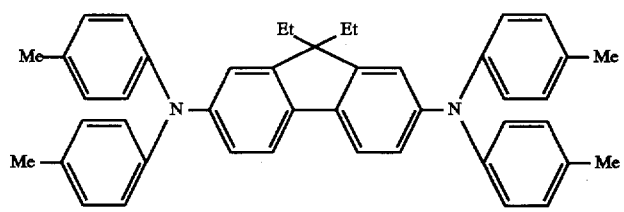
11B
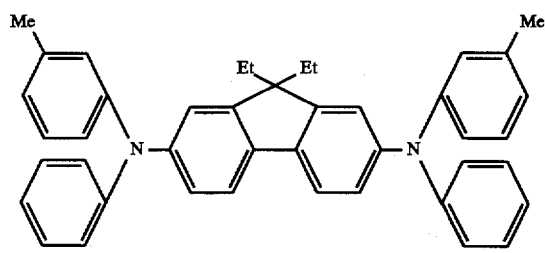
11C
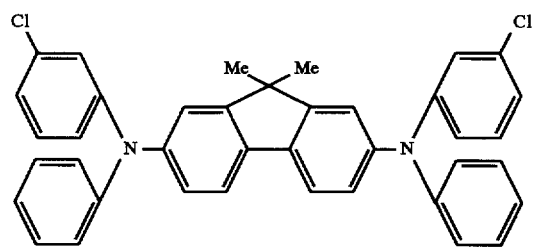
11D
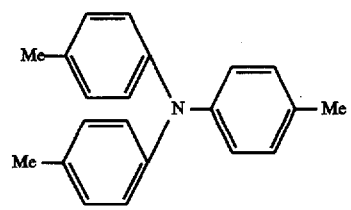
12A
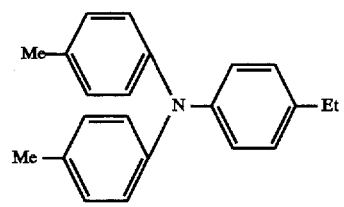
12B

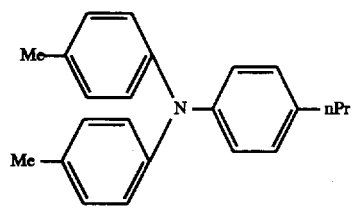  12C
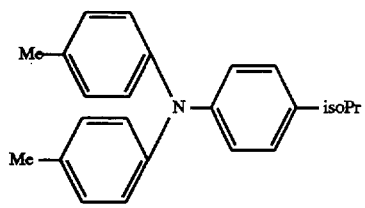  12D
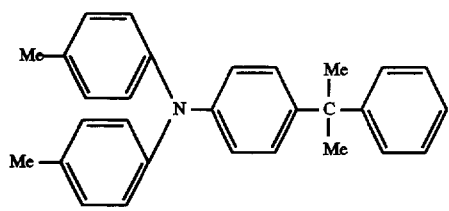  13A
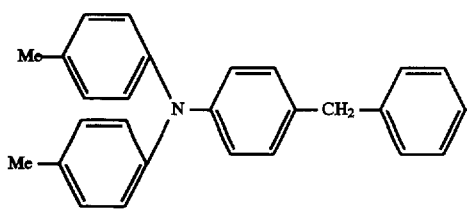  13B
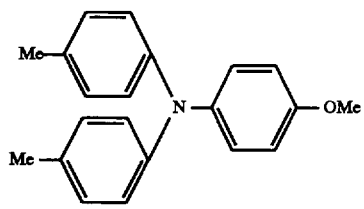  13C
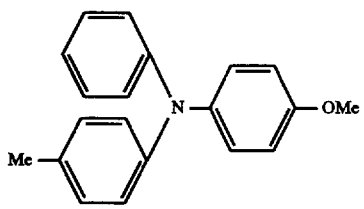  13D
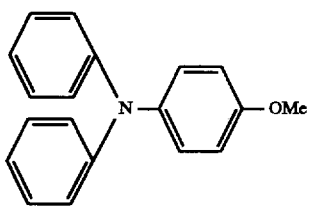  14A

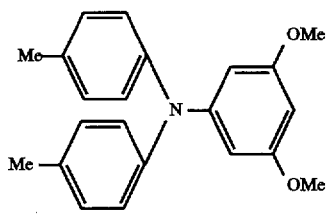
14B
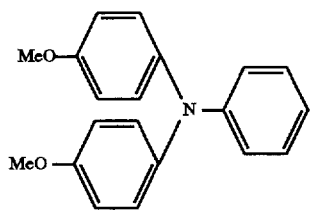
14C
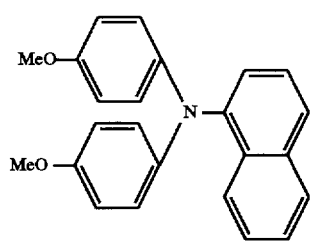
14D
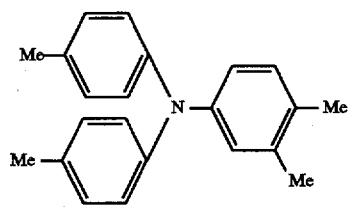
14E
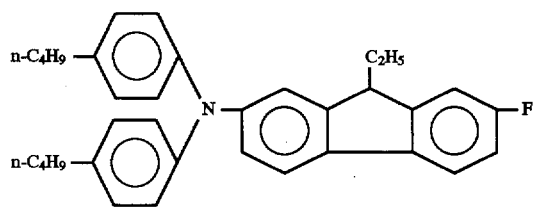
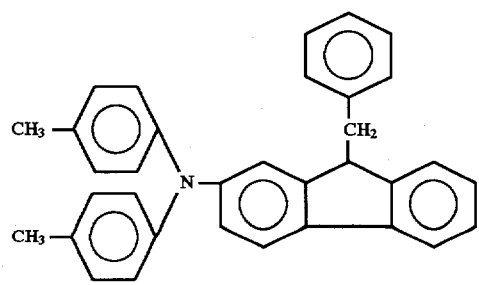
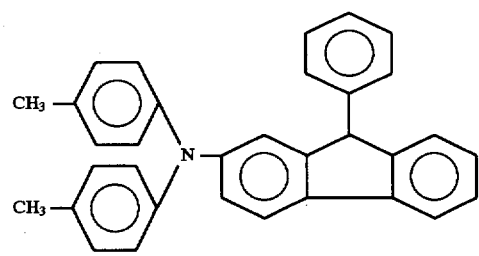

-continued
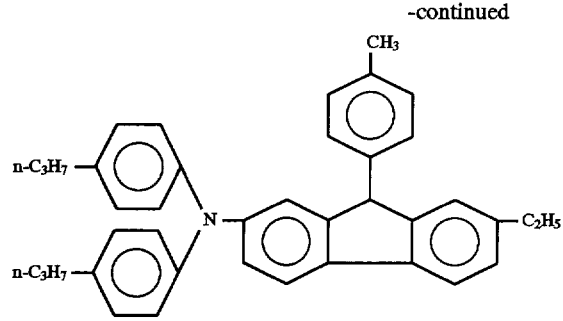
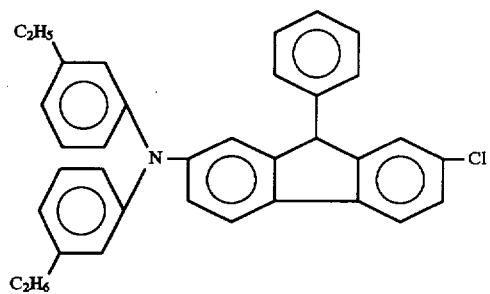
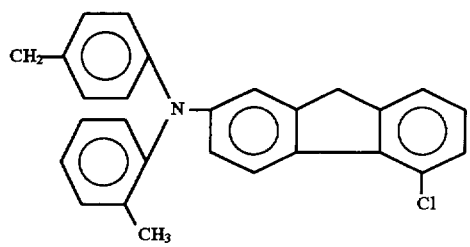
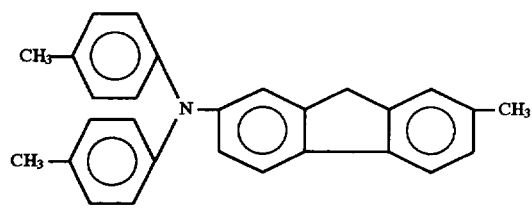
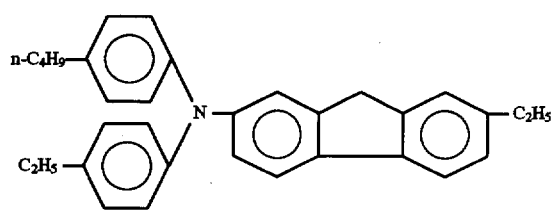
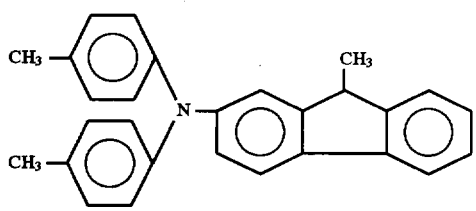

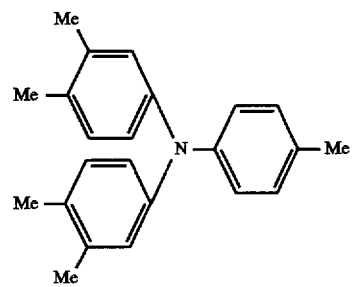
17A
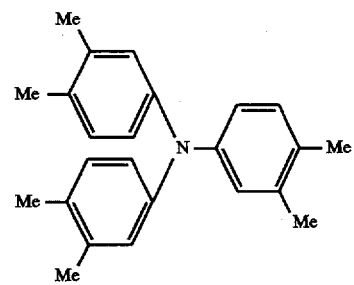
17B
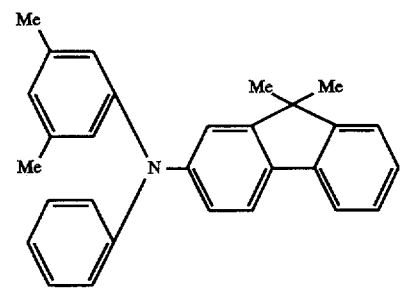
17C
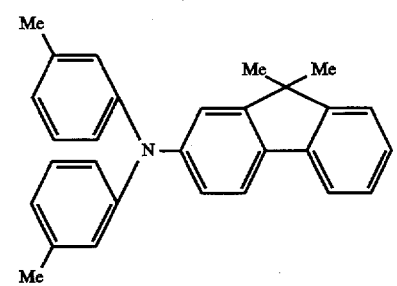
17D
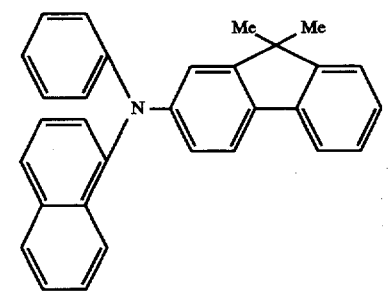
18A
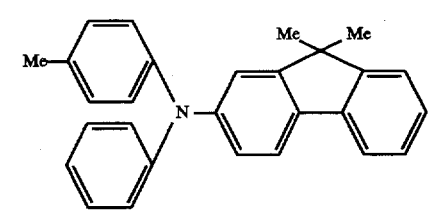
18B

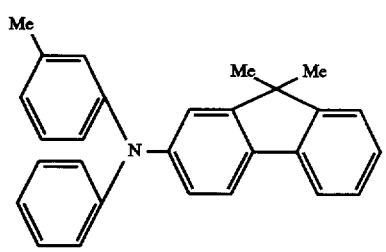

18C

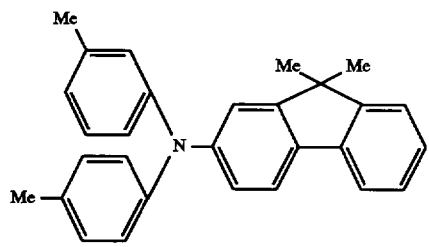

18D

Following are representative ionization and oxidation potentials for some of the aromatic substituted tertiary amines A shown above. These ionization and oxidation potentials refer to the specific compounds identified above with corresponding reference indicia.

1A—Ionization potential: 5.7 eV
1B—Oxidation potential: 0.78 V
  Ionization potential: 5.42 eV
1C—Oxidation potential: 0.81 V
  Ionization potential: 5.45 eV
3A—Oxidation potential: 0.84 V
  Ionization potential: 5.47 eV
5A Oxidation potential: 0.57 V
  Ionization potential: 5.22 eV
5B—Oxidation potential: 0.75 V
  Ionization potential: 5.40 eV
5C—Oxidation potential: 0.76 V
  Ionization potential: 5.40 eV
5D—Oxidation potential: 0.86 V
  Ionization potential: 5.49 eV
6A—Oxidation potential: 0.76 V
  Ionization potential: 5.40 eV
6B—Oxidation potential: 0.79 V
  Ionization potential: 5.43 eV
6C—Oxidation potential: 0.75 V
  Ionization potential: 5.40 eV
6D—Oxidation potential: 0.77 V
  Ionization potential: 5.41 eV
7A—Oxidation potential: 0.80 V
  Ionization potential: 5.44 eV
7B—Oxidation potential: 0.79 V
  Ionization potential: 5.43 eV
7C—Oxidation potential: 0.88 V
  Ionization potential: 5.51 eV
8A—Oxidation potential: 0.76 V
  Ionization potential: 5.40 eV
8B—Oxidation potential: 0.74 V
  Ionization potential: 5.38 eV
8C—Oxidation potential: 0.77 V
  Ionization potential: 5.41 eV
9A—Oxidation potential: 0.63 V
  Ionization potential: 5.28 eV
9B—Oxidation potential: 0.62 V
  Ionization potential: 5.27 eV
9C—Oxidation potential: 0.58 V
  Ionization potential: 5.22 eV
9D—Oxidation potential: 0.59 V
  Ionization potential: 5.23 eV
10A—Oxidation potential: 0.80 V
  Ionization potential: 5.44 eV
10B—Oxidation potential: 0.78 V
  Ionization potential: 5.43 eV
10C—Oxidation potential: 0.78 V
  Ionization potential: 5.43 eV
10D—Oxidation potential: 0.76 V
  Ionization potential: 5.41 eV
11A—Oxidation potential: 0.58 V
  Ionization potential: 5.23 eV
11B—Oxidation potential: 0.58 V
  Ionization potential: 5.23 eV
11C—Oxidation potential: 0.63 V
  Ionization potential: 5.28 eV
11D—Oxidation potential: 0.77 V
  Ionization potential: 5.41 eV
12A—Oxidation potential: 0.83 V
  Ionization potential: 5.47 eV
12B—Oxidation potential: 0.83 V
  Ionization potential: 5.47 eV
12C—Oxidation potential: 0.84 V
  Ionization potential: 5.47 eV
12D—Oxidation potential: 0.83 V
  Ionization potential: 5.47 eV
13A—Oxidation potential: 0.83 V
  Ionization potential: 5.47 eV
13B—Oxidation potential: 0 85 V
  Ionization potential: 5.48 eV
13C—Oxidation potential: 0.74 V
  Ionization potential: 5.38 eV
13D—Oxidation potential: 0.80 V
  Ionization potential: 5.44 eV 14A—Oxidation potential: 0.83 V
Ionization potential: 5.47 eV
14B—Oxidation potential: 0.84 V
Ionization potential: 5.47 eV
14C—Oxidation potential: 0.72 V
Ionization potential: 5.36 eV
14D—Oxidation potential: 0.73 V
Ionization potential: 5.38 eV
14E—Oxidation potential: 0.81 V
Ionization potential: 5.45 eV
17A—Oxidation potential: 0.78 V
Ionization potential: 5.43 eV
17B—Oxidation potential; 0.76 V
Ionization potential; 5.40 eV
17C—Oxidation potential: 0.82 V
Ionization potential: 5.46 eV
17D—Oxidation potential: 0.82 V
Ionization potential: 5.45 eV
18A—oxidation potential: 0.89 V
Ionization potential: 52 eV
18B—Oxidation potential: 0.81 V
Ionization potential: 5.45 eV
18C—Oxidation potential: 0.84 V
Ionization potential: 5.47 eV
18D—Oxidation potential: 0.79 V
Ionization potential: 5.43 eV There is no limitation as to which position on the aromatic ring of the tertiary amine that the alkoxysilane be introduced. Nor is it necessary for alkoxysilane groups to be bonded to all aromatic rings. Such determinations are made by considering factors such as solubility in the polysiloxane resin. In this case, the method of introducing a vinyl group to an aromatic ring bonded to nitrogen is to first formylate the hydrogen of the methyl group on the aromatic ring, then convert the resulted aldehyde group to the vinyl group by the Wittig reaction; thus allowing the introduction of the vinyl group as described above. It can also be produced by means of a dehydrohalogenation reaction between the hydrogen on the secondary amine and the halogenated aromatic group compound which has been substituted by the vinyl group.

The hydrogenated organic silicon compound which is able to react with the vinyl group bonded to an aromatic ring of tertiary amine A with ionization potential of 4.5–6.2 eV, is a hydrogenated organic silicon compound whose substituent on the silicon atom in its molecule is hydrogen or an alkoxy group. This compound is added to the vinyl group by a hydrosilylation reaction. Hydrogen directly bonded to silicon is an indispensable component of the hydrosilylation reaction to add to the vinyl group. Another indispensable component is a hydrolyzable group, such as an alkoxy group —$OR^3$. $R^3$ of the alkoxy group can be a short chain, i.e., 1–6 carbon atoms, such as methyl, ethyl, propyl, butyl, amyl, and hexyl; or $R^3$ can be a branched alkyl. The selection is made depending on the intended use of the product, stability during hydrosilylation, process and hydrolyzable properties.

Integer n in the formula denotes the number of alkoxy groups substituted on silicon. When n is higher than 1, the hydrophilic property of the compound is improved. When there are several groups that are able to be condensed, the compound also acts as a cross-linking agent, so the selection must be made taking into account the hardness of the resin as a result of cross-linking, as well as its hydrophilic property.

Organic group $R^2$ other than hydrogen and alkoxy which is directly bonded to the silicon atom, may be selected according to the type of substituent on the silicon atom in the polysiloxane resin, and according to the various purposes such as the solubility in the resin, reactivity for the hydrosilylation reaction, and other property adjustments of the polysiloxane resin. $R^2$ may be an alkyl group such as methyl, ethyl, propyl, butyl, amyl, and hexyl; alkenyl such as vinyl and allyl; halogenated hydrocarbon groups; aryl such as phenyl; alkaryl such as tolyl; and fluorohydrocarbon groups represented by trifluoropropyl, heptafluoropentyl, and nonafluorohexyl. If the substituent on silicon in the polysiloxane resin is methyl, the solubility is better if $R^2$ is methyl.

The polysiloxane resin is a resin soluble in organic solvents, and primarily constituting silicon-type macromolecules known as MT resins, MQ resins, T resins, and polysilsesquioxanes. Methods of manufacturing such resins are known, such as the method described on Page 17 of "Silicon-Based Polymer Science", edited by John M. Ziegler and F. W. Gordon Fearon, ACS Series 224, The American Chemical Society (1990).

The hydrosilylation reaction used in our invention may be conducted using a platinum or an organic peroxide as the catalyst. The platinum compound can be of the type used in known hydrosilylation reactions or in the preparation of addition-type silicone rubbers. The catalyst should not contain chlorine, for the reason that residual platinum chloride or chloroplatinic acid may produce hydrochloric acid during use. When added to a polysiloxane resin as an charge transporting ring substance, hydrochloric acid is a substance that inhibits the electron hole transferring function. Therefore, substances such as platinum; phosphine complexes; and substances in which platinum is supported by a carrier such as platinum/carbon, platinum/silica gel, and platinum/macromolecules, are used. The quantity of platinum catalyst used is within the range used conventionally. Thus, the quantity of platinum metal to the aliphatic unsaturated group which is the base material for hydrosilylation of 1/10 to 1/100,000 mole-ratio, would be appropriate. In the case of tertiary amines in which the aromatic ring is substituted, and taking into consideration steric hindrance, it is preferred from the standpoint of promoting the reaction, that the quantity be 1/10 to 1/10,000.

When there is a large quantity of residual platinum, however, the silicon type charge transporting material becomes brown to black. This causes photoabsorption or photodispersion when the photoelectric charge generating material in the resin layer containing the charge transporting material, or a photoelectric charge generating material through this material, is exposed to light. In addition, platinum compounds decompose when they are exposed to high temperatures, or are exposed over extended periods of time to air, thereby depositing metal particles of platinum black. Another disadvantage is that an alkoxy group in an organic alkoxysilane is easily hydrolyzed upon exposure to water to a hydroxyl group, which is easily condensed and macromolecularized by platinum. Taking these factors into consideration, it is essential to reduce the quantity of residual platinum in the silicon-type charge transportingring material. The quantity of platinum contained in the silicon-type charge transportingring material should therefore be less than 10 ppm, preferably less than 1 ppm. For purposes of our invention, the concentration of platinum compound is the concentration of platinum atoms obtained by means of atomic absorption.

Residual platinum in the silicon-type charge transporting material is adsorbed by adding adsorptive materials such as active charcoal, silica gel, and porous alumina, onto which platinum is adsorbed. Such adsorbent materials must be inert to the transporting material in the solution in which the transporting material is dissolved. The solution is then removed along with the adsorbent by filtration. The adsorbent can be used as a filler in a column, and separation can be carried out in the column. The concentration of the solution of the electron hole transfer material should preferably be less than about 50 percent by weight, but because the viscosity of such solutions may vary depending on the type of platinum catalyst used, exact ranges cannot be predicted. Similarly, the hydrosilylation reaction temperature cannot be specified, because it varies depending on the type of platinum catalyst used, its quantity, reaction groups, materials, and reaction conditions. However, from the standpoint of efficiency, it should be below the decomposition temperature of the platinum catalyst, above room temperature, and below 200° C. Considering the stability of the unsaturated aliphatic group under heat, it is desirable that the reaction temperature be below 100° C.

When using an organic peroxide as the catalyst, the only limitation is that its half-life be above room temperature. Organic peroxides which can be used are the radical polymerization initiators such as lauryl peroxide, butyl peroxide, and benzoyl peroxide.

Products of hydrosilylation reactions can be divided into two groups. In one group, the silicon atom is added to the alpha position of the vinyl group. In the other group, the silicon atom is added to the beta position of the vinyl group. The position depends on reaction conditions, such as type of vinyl compound substituent and type of catalyst used. In our invention, there is no adverse effect of a mixture of the alpha-additions and beta-additions in the hydrosilylation process. In fact, having a mixture is preferable since it prevents aggregation of charge transporting materials which tend to easily form aggregates.

The following examples illustrate our invention in more detail.

Practical Example 1

Synthesis of 4-[2-(triethoxysilyl)ethyl]triphenylamine and Synthesis of 4-(N,N-diphenylamino)benzaldehyde 101.4 g of triphenylamine and 35.5 mL of dimethyl formamide (DMF) were placed in a three-neck flask, and while stirring and cooling in ice water, 84.4 mL of phosphorus oxychloride was dropped into the flask. The temperature was raised to 95° C. The mixture was reacted for 5 hours. The reaction solution was poured into 4 L of warm water and stirred for one hour. The precipitate was collected and washed in a 1:1 mixture solution of ethanol/water. 4-(N,N-diphenylamino)benzaldehyde was obtained. The yield was 91.5 g (yield rate of 81.0%). The melting point was 128.6°–130.1° C.

Synthesis of 4-vinyltriphenylamine 14.6 g of sodium hydride and 700 mL of 1,2-dimethoxyethane were placed in a three-neck flask. While stirring at room temperature, 130.8 g of tetramethylphosphonium bromide was added. After adding one drop of anhydrous ethanol, the mixture was reacted for 4 hours at 70° C. 100 g of 4-(N,N-diphenylamino) benzaldehyde was added to the mixture. The temperature was raised to 70° C. The mixture was reacted for 5 hours. Upon completion of the reaction, the reaction solution was filtered, and an ether extract of the precipitate and the filtrate were washed in water. The ether solution was dehydrated with calcium chloride. The ether was removed and the reaction mixture was obtained. This was recrystallized from ethanol, and a needle-form, lemon-yellow 4-vinyltriphenylamine was obtained. The yield was 83.4 g (yield rate of 84.0%). The melting point was 88.5°–90.4° C.

Hydrosilylation of 4-vinyltriphenylamine 40 mL of toluene, 9.9 g (60 mmol) of triethoxysilane, and 0.018 mmol of a toluene solution of tris-(tetramethyldivinyldisiloxane) diplatinum (0, i.e., zero oxidation number of platinum in the molecule), were placed in a three-neck flask, and while stirring under room temperature, 20 mL of a toluene solution of 8.2 g of 4-vinyltriphenylamine was dropped into the flask. Upon completion of addition of drops, the mixture was stirred for 3 hours at 70° C., then diluted with 120 mL of toluene solution. The diluted solution was treated in a column filled with 200 g of dried activated charcoal for 7 hours at 140° C. in a vacuum. The toluene was removed under reduced pressure. A highly viscous lemon-yellow liquid refined material was obtained. The platinum concentration of refined material was measured by a frameless atomic absorption method using a Hitachi Polarized Zeeman Atomic Absorption Spectrophotometer. The results showed that platinum concentration of the refined material was 0.8 ppm.

Practical Example 2

Synthesis of 4-[N,N-bis-(3,4-dimethylphenyl)amino]-[2-(triethoxysilyl)ethyl]benzene and Synthesis of N,N-bis-(3,4-dimethylphenyl)aminobenzene 38.5 g (166 mmol) of 4-iodo-o-xylene, 22.9 g (166 mmol) of anhydrous potassium carbonate, and 7.0 g of copper powder were added to 20 mL of nitrobenzene, and heat-refluxed for 8 hours while stirring. The mixture was cooled, filtered, and the filtrate was removed. The reaction mixture was passed through a silica gel column, and N,N-bis-(3,4-dimethylphenyl)aminobenzene was obtained. The yield was 15.7 g (yield rate of 69%).

Synthesis of 4-[N,N-bis-(3,4-dimethylphenyl)amino] benzaldehyde 124.6 g of [N,N-bis-(3,4-dimethylphenyl)amino]benzene and 35.5 mL of DMF were placed in a three-neck flask. While stirring and cooling in ice water, 84.4 mL of phosphorus oxychloride was dropped into the flask. Upon completion of addition of drops, the mixture solution was reacted for 5 hours at 95° C., poured into 4 L of warm water, and stirred for 1 hour. The precipitate was collected and washed in a :1:1 mixture solution of ethanol/water. 4-[N,N-bis-(3,4-dimethylphenyl)amino]benzaldehyde was obtained. The yield was 107.6 g (yield rate of 79.0%).

Synthesis of 4-[N,N-bis-(3,4-dimethylphenyl) amino] styrene 12.1 g of sodium hydride and 580 mL of 1,2-dimethoxyethane were placed in a three-neck flask. While stirring at room temperature, 108.5 g of tetramethylphosphonium bromide was added. After adding one drop of anhydrous ethanol, the mixture was reacted for 4 hours at 70° C. 100 g of 4-[N,N-bis-(3,4-dimethylphenyl)amino] benzaldehyde was added to the reaction mixture. The mixture was reacted for 5 hours at 70° C. The reaction solution was filtered, and an ether extract of filtered cake and filtrate were washed in water. The ether solution was dehydrated with calcium chloride, the ether was removed, and a reaction mixture was obtained. This mixture was recrystallized twice with ethanol, and a needle-form 4-[N,N-bis-(3,4-dimethylphenyl)amino]styrene was obtained. The yield was 84.5 g (yield rate of 85.0%).

Hydrosilylation of 4-[N,N-bis-(3,4-dimethylphenyl)amino] styrene 40 mL of toluene, 6.0 g of triethoxysilane, and 0.54 mmol of a toluene solution of tris-(tetramethyldivinyldisiloxane) diplatinum (0) were placed in a three-neck flask. While stirring at room temperature, 20 mL of a toluene solution of 9.9 g of 4-[N,N-bis-(3,4-dimethylphenyl)amino]styrene was dropped into the flask. Upon completion of addition of drops, the mixture was stirred for 3 hours at 70° C. The solvent was removed under reduced pressure, and a lemon-yellow oil of 4-[N,N-bis-(3,4-dimethylphenyl)amino][2-(triethoxysilyl)ethyl]benzene was obtained. The yield was 13.4 g (yield rate of 90.1%). This refined material was subjected to the same process as in Practical Example 1, and platinum was measured in the same manner. The platinum concentration of this refined material was 1.9 ppm.

Practical Example 3

Synthesis of 4-[2-(triethoxysilyl)ethyl]triphenylamine and Synthesis of 4-(N,N-diphenylamino)benzaldehyde 101.4 g of triphenylamine and 35.5 mL of DMF were placed in a three-neck flask. While stirring and cooling in ice water, 84.4 mL of phosphorus oxychloride was dropped into the flask. The temperature was increased to 95° C. and the mixture was reacted for 5 hours. 4 L of warm water was poured into the flask and the mixture was stirred for one hour. A precipitate was collected and washed in a 1:1 mixture solution of ethanol/water. 4-(N,N-diphenylamino) benzaldehyde was obtained. The yield was 91.5 g (yield rate of 81.0%), and the melting point was 128.6°–130.1° C.

Synthesis of 4-vinyltriphenylamine 14.6 g of sodium hydride and 700 mL of 1,2-dimethoxyethane were placed in a three-neck flask. While stirring at room temperature, 130.8 g of tetramethylphosphonium bromide was added. After adding one drop of anhydrous ethanol, the mixture was reacted for 4 hours at 70° C. 100 g of 4-(N,N-diphenylamino) benzaldehyde was added to the mixture. The temperature was raised to 70° C. and the mixture was reacted for 5 hours. Upon completion of the reaction, the reaction solution was filtered. An ether extract of the precipitate and the filtrate were washed in water. The ether solution was dehydrated with calcium chloride, the ether was removed, and a reaction mixture was obtained. The reaction mixture was recrystallized from ethanol, and a needle-form, lemon-yellow 4-vinyltriphenylamine was obtained. The yield was 83.4 g (yield rate of 84.0%), and the melting point was 88.5°–90.4° C.

Hydrosilylation of 4-vinyltriphenylamine 40 mL of toluene, 9.9 g (60 mmol) of triethoxysilane, and 0.018 mmol of a toluene solution tris-(tetramethyldivinyldisiloxane) diplatinum(0) were placed in a three-neck flask. While stirring under room temperature, 20 mL of a toluene solution of 8.2 g of 4-vinyltriphenylamine was dropped into the flask. Upon completion of addition of drops, the mixture was stirred for 3 hours at 70° C., cooled to room temperature, and then the reaction mixture was diluted with 110 mL of toluene solution. The diluted solution was subjected to the same process as in Practical Example 1, and platinum was measured in the same manner. The platinum concentration was 1.9 ppm.

It should be apparent from the above, that our invention provides electron hole transferring materials which are soluble in polysiloxane resins. These material are transparent when mixed with such resins. These features provide superiority in hardness and environmental resistance, which allows their application as low surface energy polysiloxane organic photoconductive resins. Our silicon-type electron hole transferring materials are useful not only in electrophotographic processes such as photocopiers and laser beam printers, but also as electric charge transfer layers, necessary in construction of organic electroluminescent elements.

Other variations may be made in compounds, compositions, and methods described herein without departing from the essential features of our invention The forms of our invention are exemplary only and not limitations on its scope as defined in the appended claims.

We claim:

1. A method of manufacturing a silicon-type charge transporting material of a formula A—$[R^1SiR^2_{3-n}Q_n]_p$ wherein A is an aromatic substituted tertiary amine having a plurality of aromatic groups and A represents an organic group derived from a compound having charge transporting properties and an ionization potential within the range of 4.5–6.2 eV; $R^1$ is an alkylene group of 1–18 carbon atoms; $R^2$ is a monovalent hydrocarbon group or a monovalent halogen-substituted hydrocarbon group of 1–15 carbon atoms; Q is a hydrolyzable group; and n and p each is 1–3;

the silicon-type charge transporting material is an aromatic substituted tertiary amine having a plurality of aromatic groups, and a silyl group containing the hydrolyzable group Q;

the method comprising introducing, by means of a hydrocarbon group in the presence of a hydrosilylation platinum compound as a catalyst, the silyl group into an aromatic ring of at least one of the aromatic groups of the component A of the formula compound having charge transporting properties and ionization potential within the range of 4.5–6.2 eV;

contacting the silicon-type charge transporting material with an adsorbent for the platinum compound and adsorbing the platinum compound onto the adsorbent; and separating the platinum compound and the adsorbent from the silicon-type charge transporting material, so that the concentration of residual platinum compound in the silicon-type charge transporting material is less than 10 ppm.

2. The method according to claim 1 wherein hydrolyzable group Q is an alkoxy group.

3. The method according to claim 2 wherein some or all of the aromatic groups of the compound have charge transporting properties and a substituent in the form of an unsaturated hydrocarbon group, which includes subjecting the substituent to hydrosilylation with an alkoxysilane, to obtain silicon-type charge transporting materials of the formula A—$[R^1SiR^2_{3-n}Q_n]_p$.

4. The method according to claim 1 in which the adsorbent is inert with respect to the silicon-type charge transporting material.

5. The method according to claim 4 in which the adsorbent is selected from the group consisting of activated charcoal, silica gel, and porous alumina.

6. The method according to claim 1 further comprising dissolving the silicon-type charge transporting material into a solution with an adsorbent, contacting the solution with the adsorbent and separating the platinum compound from the silicon-type charge transporting material by passing the solution through a column filled with the adsorbent.

7. A silicon-type charge transporting material made according to the method defined in claim 1.

8. A method of manufacturing a silicon-type charge transporting material A—$[R^1SiR^2_{3-n}Q_n]_p$ wherein A is an aromatic substituted tertiary amine with a plurality of aromatic groups and wherein A is an organic group derived from a compound having charge transporting properties and an ionization potential within the range of 4.5–6.2 eV; $R^1$ is an alkylene group of 1–18 carbon atom; $R^2$ is a monovalent hydrocarbon group or a monovalent halogen-substituted hydrocarbon group of 1–15 carbon atoms; Q is a hydrolyzable group; and n and p are each 1–3;

the method comprising introducing, in the presence of a hydrosilylation platinum compound as catalyst, a hydrocarbon group between an aromatic ring of the compound of the formula component A having charge transporting properties and containing a vinyl group substituted onto the aromatic ring, and a silicon atom of an organic silicon compound with a hydrogen atom bonded to silicon;

contacting the silicon-type charge transporting material with an adsorbent for the platinum compound and adsorbing the platinum compound onto the adsorbent; and separating the platinum compound and the adsorbent from the silicon-type charge transporting material, so that the concentration of residual platinum compound in the silicon-type charge transporting material is less than 10 ppm.

9. The method according to claim 8 in which the adsorbent is inert with respect to the silicon-type charge transporting material.

10. The method according to claim 9 in which the adsorbent is selected from the group consisting of activated charcoal, silica gel, and porous alumina.

11. The method according to claim 8 in which the silicon-type charge transporting material is contacted with the adsorbent as a solution in which the silicon-type charge transporting material has been dissolved, and the platinum compound is separated from the silicon-type charge transporting material by passing the solution through a column filled with the adsorbent.

12. A silicon-type charge transporting material made according to the method defined in claim 8.

* * * * *